United States Patent [19]
Yano et al.

[11] Patent Number: 5,107,851
[45] Date of Patent: Apr. 28, 1992

[54] NON-CONTACT TONOMETER

[75] Inventors: Koichi Yano, Kawasaki; Koji Uchida, Yokohama; Shinya Tanaka, Tokyo, all of Japan

[73] Assignee: Canon Kabushiki Kaisha, Tokyo, Japan

[21] Appl. No.: 731,485

[22] Filed: Jul. 17, 1991

Related U.S. Application Data

[63] Continuation of Ser. No. 408,238, Sep. 18, 1989, abandoned.

[30] Foreign Application Priority Data

Sep. 22, 1988 [JP] Japan .................. 63-239189
Sep. 22, 1988 [JP] Japan .................. 63-239190

[51] Int. Cl.$^5$ .................................................. A61B 3/16
[52] U.S. Cl. ..................................... 128/648; 128/652
[58] Field of Search ........................ 128/645, 648, 652

[56] References Cited

U.S. PATENT DOCUMENTS 3,585,849  6/1971  Grolman ............... 128/648
4,665,923  5/1987  Kobayashi ............ 128/648
4,951,670  8/1990  Tanaka .................. 128/648

FOREIGN PATENT DOCUMENTS 0164730  12/1985  European Pat. Off. ........ 128/645
63-300740 12/1988  Japan .
2175412  11/1986  United Kingdom .

Primary Examiner—Randy C. Shay
Attorney, Agent, or Firm—Fitzpatrick, Cella, Harper & Scinto

[57] ABSTRACT

A non-contact tonometer has a fluid projecting device for compressing fluid in a compression chamber and projecting the fluid to the cornea of an eye to be examined located at a predetermined distance therefrom. The fluid injecting device is capable of selecting a first range as a pressurizing range for measurement of intraocular tension and a second range including a value higher in the degree of pressurization relative to the first range. The tonometer also includes a measuring device for detecting a predetermined deformation of the cornea of the eye to be examined caused by the compressed fluid and measuring the value of the intraocular tension of the eye to be examined, a change-over device for changing over the pressurizing range for measurement of intraocular tension between the first range and the second range, a state detecting device for effecting at least one of the detection of the fact that measurement is impossible by the measuring device and the detection of the replacement of the eye to be examined by another eye, and a control device for operating the change-over device on the basis of at least one of the output of the state detecting device and the measured value measured by the measuring device.

14 Claims, 6 Drawing Sheets

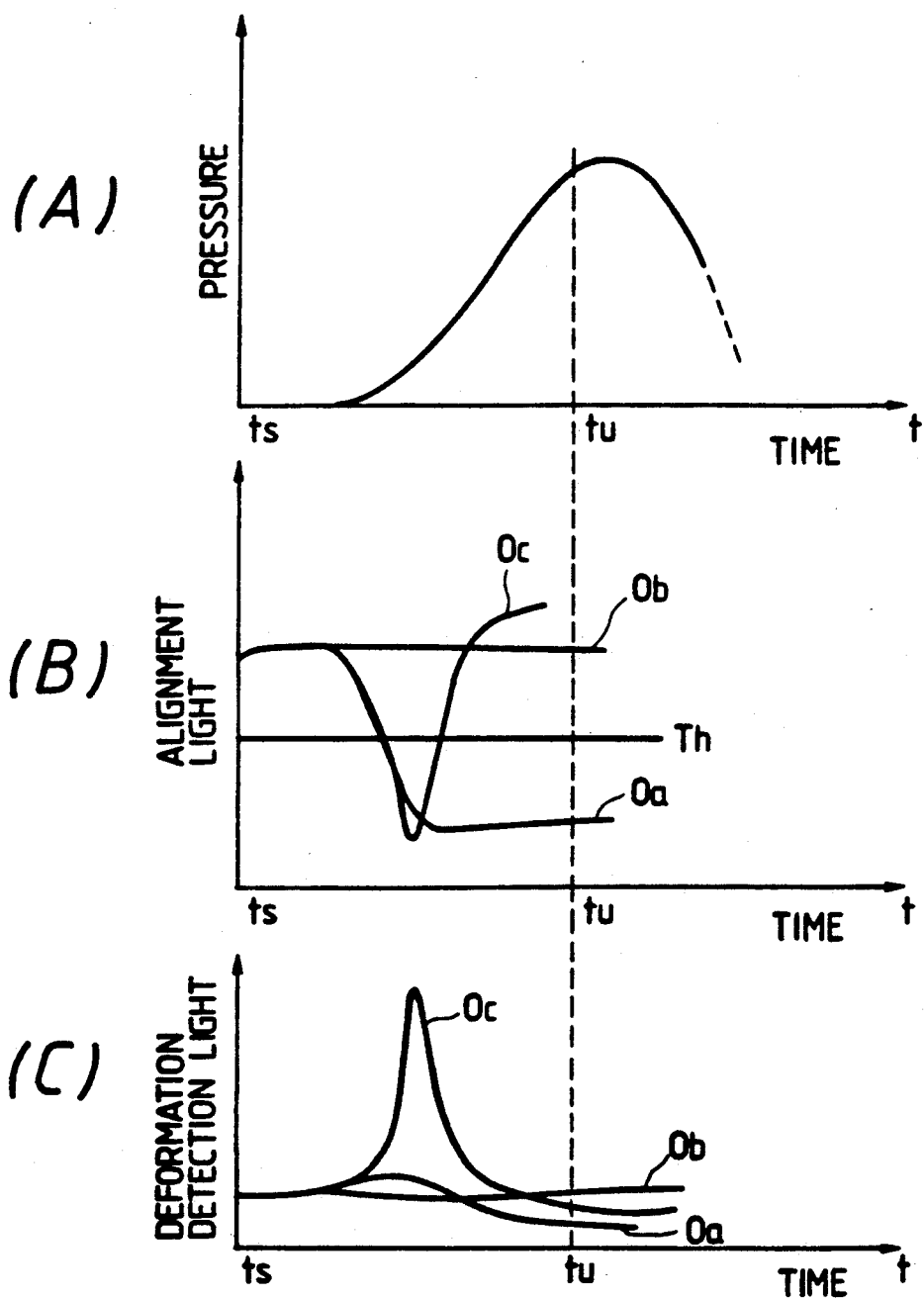

NON-CONTACT TONOMETER

This application is a continuation of application Ser. No. 07/408,238 filed Sep. 18, 1989 now abandoned.

BACKGROUND OF THE INVENTION

1. Field of the Invention

This invention relates to a non-contact tonometer which blows compressed fluid to an eye onto be examined to thereby deform the cornea of the eye and detects a predetermined deformed state thereof and measures the intraocular pressure of the eye to be examined.

2. Related Background Art

Heretofore, in a non-contact tonometer of this kind, compressed air has generally been used as compressed fluid. For example, as disclosed in U.S. Pat. No. 3,585,849 and European Patent No. 164,730, the air in a compression chamber is gradually compressed by a piston driven by a solenoid, and the compressed air is projected to the cornea of an eye to be examined through a nozzle and the time until the cornea becomes applanate or the internal pressure of the compression chamber when the cornea has become applanate is measured, whereafter the supply of electrical power to the nozzle is cut off. Also, in the non-contact tonometer of this kind, the measurement range is set to the order of 100 mmHg at the greatest so that even high intraocular pressure of great strength can be measured.

However, in most of ordinary eyes to be examined, the intraocular pressure is of the order of 30 mmHg at the highest and therefore, an apparatus which projects compressed fluid under more than the necessary pressure to the cornea and thereby avoids imparting excessive discomfort to the examinee has also been proposed in Japanese Laid-Open Patent Application No. 63-300740.

However, in the above-described example of the prior art, for a certain eye to be examined, change-over is effected to the measurement range for high intraocular pressure and measurement is effected. Thereafter, even if another eye is to be examined, the measurement range for low intraocular pressure is not restored as long as a particular range change-over switch is not depressed. Thus, measurement is effected in the measurement range for high intraocular pressure and if the next eye to be examined is of intraocular pressure in a range measurable in the measurement range for low intraocular pressure, excess air will be supplied to the eye to be examined to thereby impart discomfort to the examinee.

Also, in the above-described example of the prior art, in the case of an eye to be examined having high intraocular pressure exceeding this range, predetermined deformation of the cornea is not obtained as a matter of course when such eye is measured in a low measurement range and thus, measurement becomes impossible.

At this time, it is very difficult to distinguish whether the cause of the impossibility of measurement is due to an improper range of the compression pressure or unsatisfactory alignment caused by movement or blinking of the eye to be examined during measurement.

SUMMARY OF THE INVENTION

It is an object of the present invention to provide a non-contact tonometer designed not to supply excess fluid to the cornea of an eye to be examined and not to impart discomfort to the examinee.

It is another object of the present invention to provide a non-contact tonometer which is provided with a measurement range for low intraocular pressure and which, for an eye of high intraocular pressure, is changed over to a measurement range for high intraocular pressure.

It is still another object of the present invention to provide a non-contact tonometer which, in the case of unsatisfactory alignment, does not mistake an eye of low intraocular pressure for an eye of high intraocular pressure and does not change over the measurement range to a measurement range for high intraocular pressure.

It is yet still another object of the present invention to provide a non-contact tonometer which, for the same object, changes the measurement range during the next measurement in a case where the measured value is high beyond the measurement range when measurement is effected in a measurement range for low intraocular pressure or in a case where the measured value is sufficiently low when measurement is effected in a measurement range for high intraocular pressure.

BRIEF DESCRIPTION OF THE DRAWINGS

FIG. 2(A) is a graph of the internal pressure of a compression chamber.

FIG. 2(B) is a graph of an alignment light output.

FIG. 2(C) is a graph of a cornea deformation detection light output.

DESCRIPTION OF THE PREFERRED EMBODIMENTS

Figure 1:
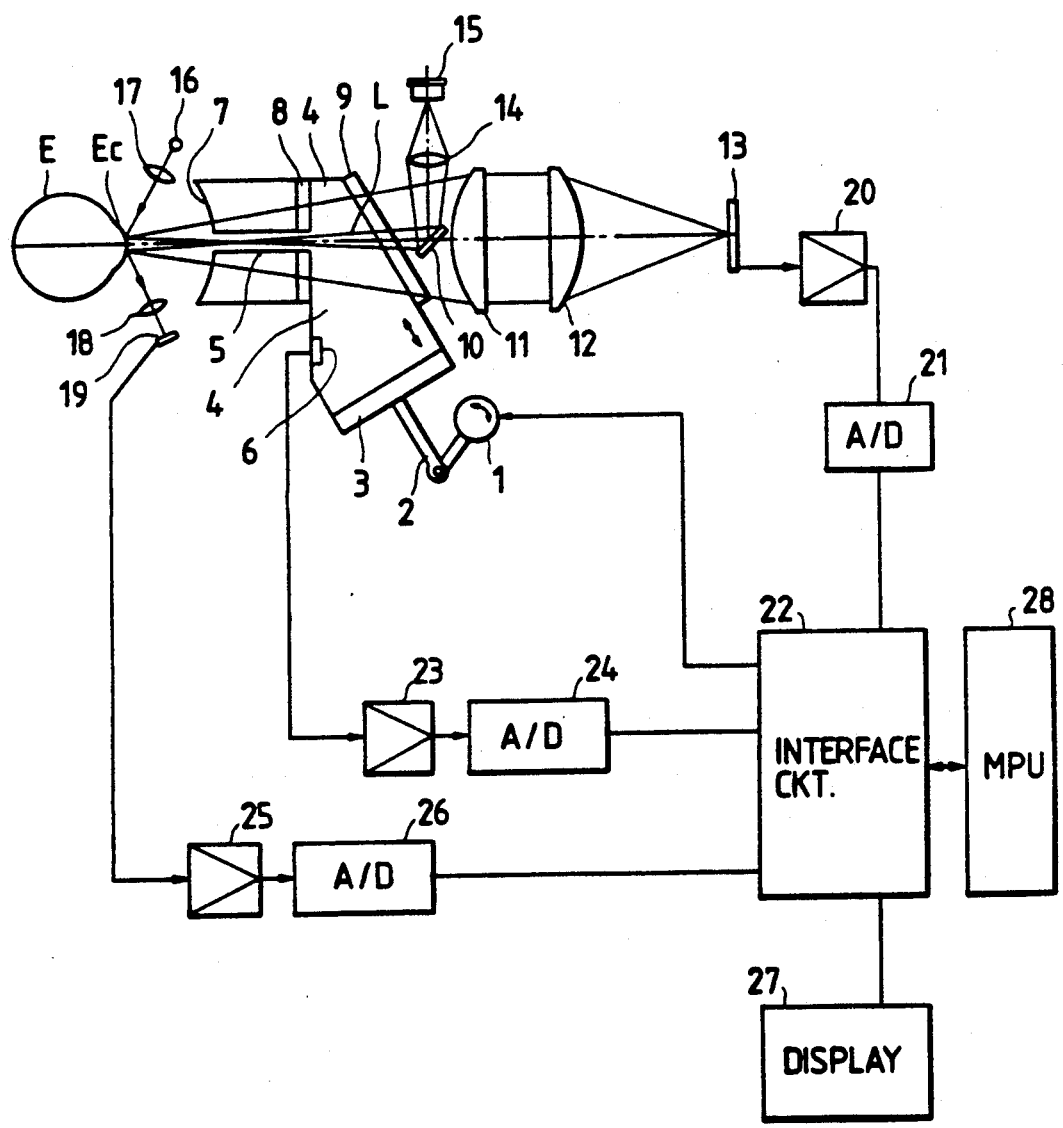
FIG. 1 shows the construction of a first embodiment of the present invention.

Referring to FIG. 1 which shows a first embodiment of the present invention, a piston 3 driven by a solenoid 1 through a crank 2 may be advanced into a compression chamber 4 to compress the air in the compression chamber 4 and the compressed air may be blown against the cornea Ec of an eye E to be examined through a nozzle 5. A pressure sensor 6 is provided in the compression chamber 4. A concave mirror 7 is provided forwardly of the nozzle 5, and this concave mirror 7 is a concave dichroic mirror reflecting visible light and transmitting near-infrared light therethrough and is designed to form the image of the front eye part of the eye E to be examined on the fundus of the eye E to be examined. Transmitting windows 8 and 9 made of a transparent material are provided in a portion corresponding to the optical path L rearward of the nozzle 5, which is mounted on the central portion of the transmitting window 8. A dichroic mirror 10 transmitting visible light therethrough and reflecting near-infrared light, lenses 11 and 12 and a photosensor 13 are successively arranged on the optical path L behind the transmitting window 9. A lens 14 and an infrared light source 15 for alignment such as an infrared light emitting diode are disposed on the optic axis of the reflection side of the dichroic mirror 10. A light source 16 and a lens 17 are provided in a direction oblique with respect to the eye E to be examined, and the reflected light of the light beam from the light source 16 on the front eye part of the eye E to be examined may be detected by a lens 18 and a photosensor 19. Further, the output of the photosensor 13 is connected to an A/D converter 21 through an amplifier 20, and the output of the A/D converter 21 is connected to an interface 22. Also, the output of the pressure sensor 6 is connected to the interface 22 through an amplifier 23 and an A/D converter 24, and the output of the photosensor 19 is connected to the interface 22 through an amplifier 25 and an A/D converter 26. The output of the interface 22 is connected to the solenoid 1 and a display device 27, and a signal may be given and taken between the interface 22 and MPU (microprocessor unit) 28.

The light beam emitted from the infrared light source 15 is condensed near the exit of the nozzle 5 through the lens 14 and the dichroic mirror 10 transmits visible light therethrough and reflects near-infrared light. Thereafter the light beam diverges again and is reflected by the cornea Ec of the eye E to be examined, whereafter it passes through the concave dichroic mirror 7 reflecting visible light and transmitting near-infrared light therethrough and passes through the transmitting windows 8 and 9 and is condensed on the photosensor 13 by the lenses 11 and 12. The output of the photosensor 13 is digitalized through the A/D converter 21. That is, the amount of deviation of the alignment between the direction of the nozzle 5 and the optic axis L1 of the eye E to be examined is detected by the light reception level of the cornea-reflected image of the infrared light source 15.

In the intraocular pressure measuring means, the piston 3 is driven by the rotational solenoid 1 through the crank 2, whereby the air in the compression chamber 4 is compressed and the internal pressure thereof is detected by the pressure sensor 6. The compressed air passed through the nozzle 5, deforms the cornea Ec of the eye E to be examined, and the predetermined deformation, e.g. applanation, of the cornea Ec is detected when a maximum quantity of light enters the photosensor 19 which receives the light beam from the light source 16. For example, the light source 16 and the photosensor 19 are provided at the focus positions of the lenses 17 and 18, respectively, and the output of the photosensor 19 is digitalized by the A/D converter 26 through the amplifier 25. The output value of the pressure sensor 6 when the output of the photosensor 19 becomes maximum is also digitalized by the A/D converter 24 through the amplifier 23, and by the use of a conversion equation obtained in advance from this value, the value of the intraocular pressure is calculated in the MPU 28.

The MPU 28 has a program timer and prescribes awaiting time. That is, when the predetermined cornea deformation signal from the photosensor 19 is not obtained even if the waiting time passes after the supply of electrical power to the solenoid 1 is started, measurement is determined to be impossible and an error indication is displayed on the display device 27.

Here, two cases are conceivable as the cause of the aforementioned impossibility of measurement. The first case is a case where the cornea deformation signal has not been obtained due to an alignment deviation or blinking, and in this case, there is a high probability that measurement becomes possible if measurement is effected again. The second case is a case where the compressed air itself could not fundamentally cause cornea deformation due to the high intraocular pressure of the eye E to be examined. In this case, even if measurement is effected again, measurement becomes impossible as long as the eye to be examined is the same eye. At this time, on the basis of a detection signal from the photosensor 19 indicative of the impossibility of measurement, the energy imparted to the solenoid 1 must be made greater, that is, the pressure range must be changed, through the amplifier 25, the A/D converter 26 and the interface 22 from the next measurement, whereby air of higher pressure must be made. Distinguishing between these two is indispensable because it is greatly concerned in the probability of the success of the next measurement.

FIGS. 2(A), (B) and (C) are graphs concerning two examples in which a measurement error has been determined as previously described and one example of a normal measurement. FIG. 2(A) is a graph of the output of the pressure sensor 6 and time t, FIG. 2(B) is a graph of the output of the photosensor 13 for alignment and time t, and FIG. 2(C) is a graph of the output of the photosensor 19 for cornea deformation detection and time t.

In these graphs, ts indicates the measurement starting point of time, and tu indicates the to waiting time, and here, as shown in FIG. 2(A), it is to be understood that the air in the compression chamber 4 has been compressed. Oa shows the case of an error which has been caused by alignment deviation during measurement, Ob shows the case of a range-over error (an error due to the range of pressure being unsuitable to the eye to be examined) and Oc shows the case of a normal measurement. At the measurement starting point of time ts, the graph shows the output of the alignment light and the output of the deformation detection light and both Oa, Ob and Oc and there is no appreciable difference therebetween. However, when as shown by Oa, alignment deviation has been caused during measurement and the output of the alignment light has dropped rapidly, the deformation light output also remains small until the waiting time tu. When as shown by Ob, the measurement range is originally unsuitable for the eye E to be examined, even if the air in the compression chamber 4 is gradually compressed as shown in FIG. 2(A), the output of the cornea deformation detection light is not obtained from the photosensor 19. However, the difference of this case from Oa is that the output of the alignment light remains at predetermined level. If the pressure is gradually increased for 0c in the case of normal measurement, the cornea Ec becomes applanate and the output of the cornea deformation detection light has a certain peak as shown in FIG. 2(C) when a pressure corresponding to the intraocular pressure is reached. With this occurs, the output of the alignment light conversely drops suddenly, but when the cornea is restored its original convex state, the alignment light again restores its original output level.

As described above, whether measurement has been effected properly can be determined by detecting the output level of the output of the cornea deformation detection light by the MPU 28. If the output level still maintains a small level even at the waiting time tu, and if the level of the alignment light is smaller than at that point in time tu a predetermined level Th, it is determined to be a measurement error caused by alignment deviation. If the level is greater than the predetermined level Th, it is determined to be a measurement error caused by range-over, and thus, a distinction between these two errors becomes possible.

Figure 3A:
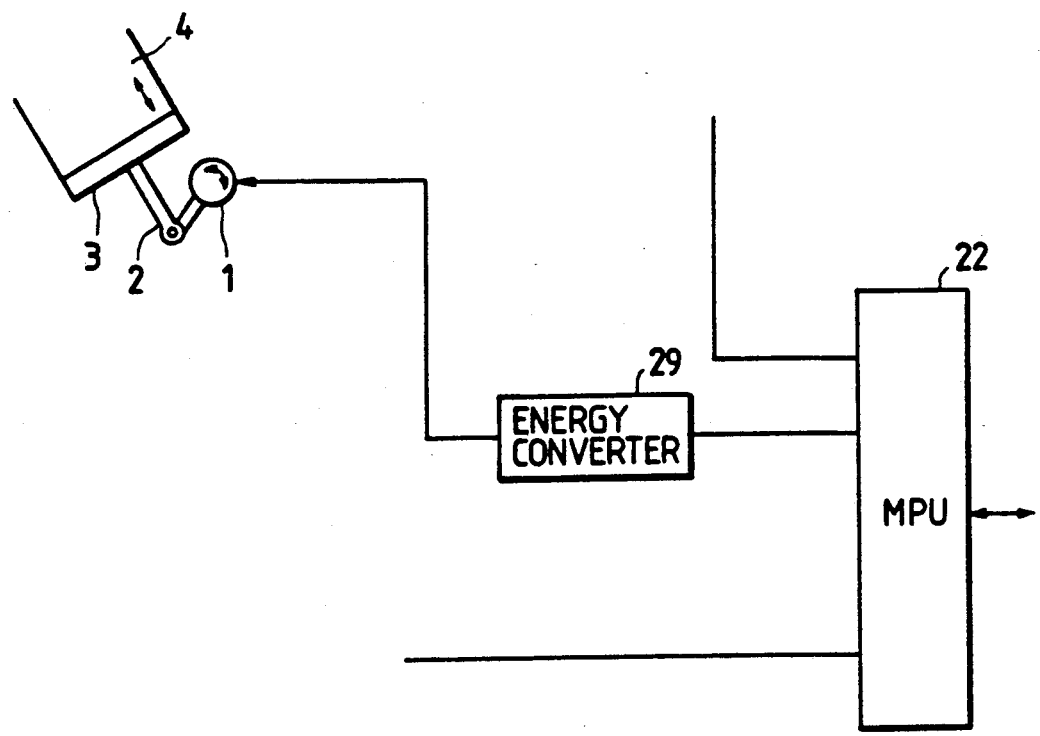
FIGS. 3A and 3B show a specific example of the range change-over.
Figure 3B:
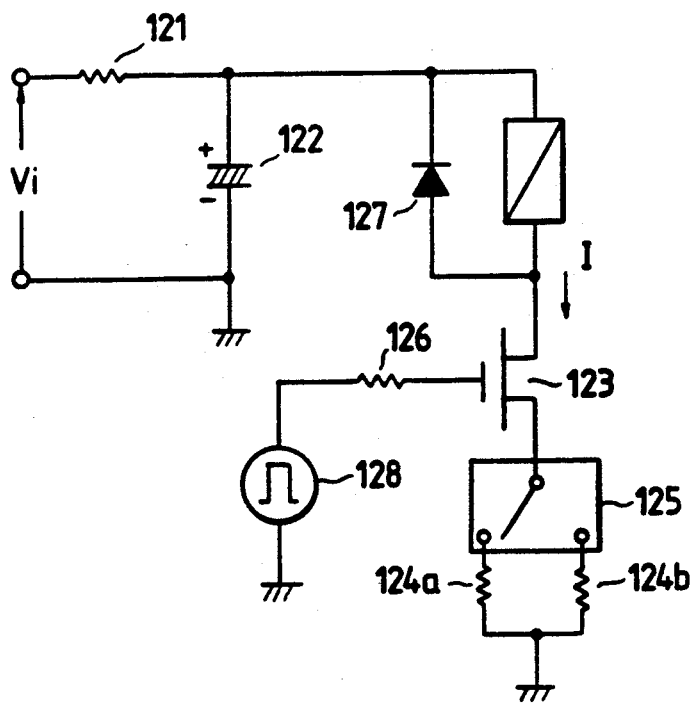

FIGS. 3A and 3B show a second embodiment of the present invention. The difference between this embodiment and the embodiment of FIG. 1 is that an energy converter circuit 29 is interposed between the interface 22 and the solenoid 1 in this embodiment. A specific form of this energy converter circuit 29 is described in detail in Japanese Laid-Open Patent Application No. 63-300740. That is, FIG. 3B shows an example of the control circuit for controlling the torque of the solenoid 2, and a charging resistor 121 and an electrolytic condenser 122 are provided to supply a 0C power source for the solenoid 2, and the two source resistors 124a and 124b of an MOS type field effect transistor 123 may be changed over to thereby increase or decrease the electric current I supplied to the solenoid 2. In FIG. 3B, the reference numeral 125 designates a switch for changing over the source resistors 124a and 124b, the reference numeral 126 denotes the gate resistor of the transistor 123, the reference numeral 127 designates a surge absorbing diode, and the reference numeral 128 denotes a constant voltage circuit for providing a gate voltage in the form of pulse.

In the case of FIG. 3B, it is possible to charge the electrolytic condenser 122 from an applied voltage Vi through the charging resistor 121, and control the electric current flowing to the solenoid 2, correspondingly to the source resistor 124a or 124b selected by the switch 125.

Here, when the cause of the impossibility of measurement is a range-over caused due to the intraocular pressure of the eye E to be examined being too high and deformation of the cornea fails to be caused, the energy converter circuit 29 may be controlled by the output of the interface 22 so that greater energy may be imparted to the solenoid 1, whereby measurement of the even higher intraocular pressure becomes possible during the next measurement.

Figure 4:
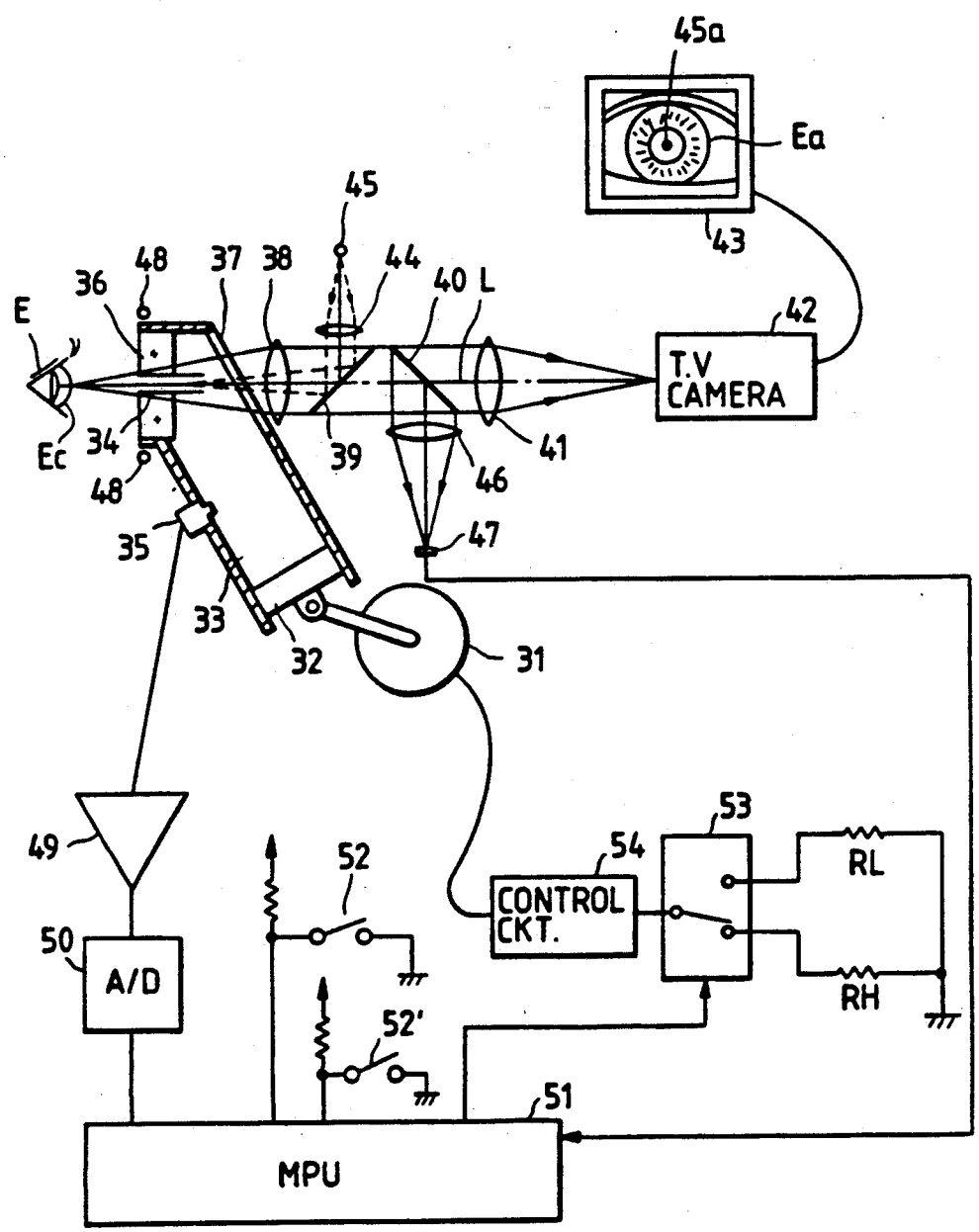
FIG. 4 shows the construction of a second embodiment of the present invention.

Referring to FIG. 4 which shows a second embodiment of the present invention, a piston 32 driven by a solenoid 31 may be advanced into a compression chamber 33 to compress the air in the compression chamber 33, and the compressed air may be blown against the cornea Ec of an eye E to be examined through a nozzle 34. A pressure sensor 35 is provided to measure the internal pressure of the compression chamber 33. Transparent windows 36 and 37 made of a transparent material are provided in the portion of the compression chamber 33 which corresponds to the optical path L, and the nozzle 34 is mounted on the central portion of the transparent window 36. Behind an objective lens 38, half-mirrors 39 and 40 are obliquely disposed on the optical path L behind the transparent window 37, and further, an imaging lens 41 and a television camera 42 are successively arranged, and the output of the television camera 42 is connected to a television monitor 43. A lens 44 and an infrared light source 45 for alignment such as an infrared light emitting diode are disposed on the optic axis of the reflection side of the half-mirror 39, and a lens 46 and a light receiving sensor 47 are disposed on the optic axis of the reflection side of the half-mirror 40. The light receiving sensor 47 is disposed so that the quantity of incident light becomes greatest when the cornea Ec becomes applanate. A plurality of light emitting elements 48 for illuminating the external eye are provided around the transparent window 36. The output of the pressure sensor 35 is connected to MPU (microprocessor unit) 51 through an amplifier 49 and an A/D converter 50. The output of a reset switch 52 is connected to the MPU 51, the output of which is connected to an analog switch 53. The analog switch 53 operates so as to alternatively connect a source resistor RL or RH to a solenoid control circuit 54 for driving the solenoid 31. Also, the output of the light receiving sensor 47 is connected to the MPU 51 so that as shown in FIG. 1, the impossibility of measurement is detected and the driving of the solenoid can be controlled.

At first, the examiner carries out alignment by observing the image Ea of the eye to be examined formed on the television camera 42 through the objective lens 38 and the imaging lens 41 and the light source image 45a emitted from the infrared light source 45 and reflected by the cornea Ec on the television monitor 43, and when this alignment is completed, the solenoid 31 is automatically or manually energized. So, as previously described, the piston 32 is driven by the solenoid 31 and the air in the compression chamber 33 is compressed and is projected from the nozzle 34 to the cornea Ec, which thus begins to be deformed. When the cornea Ec becomes applanate, the quantity of light entering the light receiving sensor 47 becomes greatest and therefore, the pressure in the compression chamber 33 when the output of the light receiving sensor 47 has reached its peak is directly detected by the pressure sensor 35, and by the use of the value of this internal pressure, the intraocular pressure is measured from a pressure conversion equation prepared in advance. Also, the change-over of the measurement range becomes possible by changing over the source resistors RL and RH of the field effect type transistor included in the solenoid control circuit 54 for controlling the electric current supplied to the solenoid 31, by the analog switch 53.

Here, let it be assumed that the relation between the two source resistors RL and RH is RH>RL and the intraocular pressure has been measured with the source resistance tentatively set to RH. If in this case, the intraocular pressure converted on the basis of the result of A/D-converting the output from the pressure sensor 35 by the A/D converter 50 is over the measurement range, the MPU 51 controls the analog switch 53 from the next measurement so that the source resistor RH is automatically changed over to RL and more electric current flows to the solenoid 31.

Conversely, if the measured value obtained when the source resistance is set to RL is within a range which can be measured even by the source resistor RH, the source resistance is likewise automatically set to RH by the command of the MPU 51 so that no excess shock may be imparted to the eye E to be examined from the next time.

Here, in the present embodiment, when the examinee is replaced by another examinee, the examiner closes the reset switch 52 to thereby automatically return the measurement range to the initial setting before the measurement of the next examinee. The reset switch 52 may serve also as a printing switch for a printer or other functional switch such as a switch for clearing the intraocular pressure data in the past, whereby the cumbersomeness of the switch operation can be mitigated at any rate. This is a very important function when it is considered that in the case of the measurement of intraocular pressure, almost all eyes to be examined are of normal intraocular pressure and with regard to an eye of high intraocular pressure, an attempt is made to reduce the intraocular pressure of such eye on the spot by the use of a medicine and therefore the probability with which measurement can be accomplished in a low range is considerably high. That is, it is more popular to select a low range as the initial setting.

Also, even in the same examinee, the value of intraocular pressure may vary depending on the eye to be examined and therefore, it is desirable to return the measurement range to the initial setting each time the switching of the eye to be measured is detected by a microswitch 52' for detecting the movement of a stage which means the switching of the left and right eyes.

Figure 5:
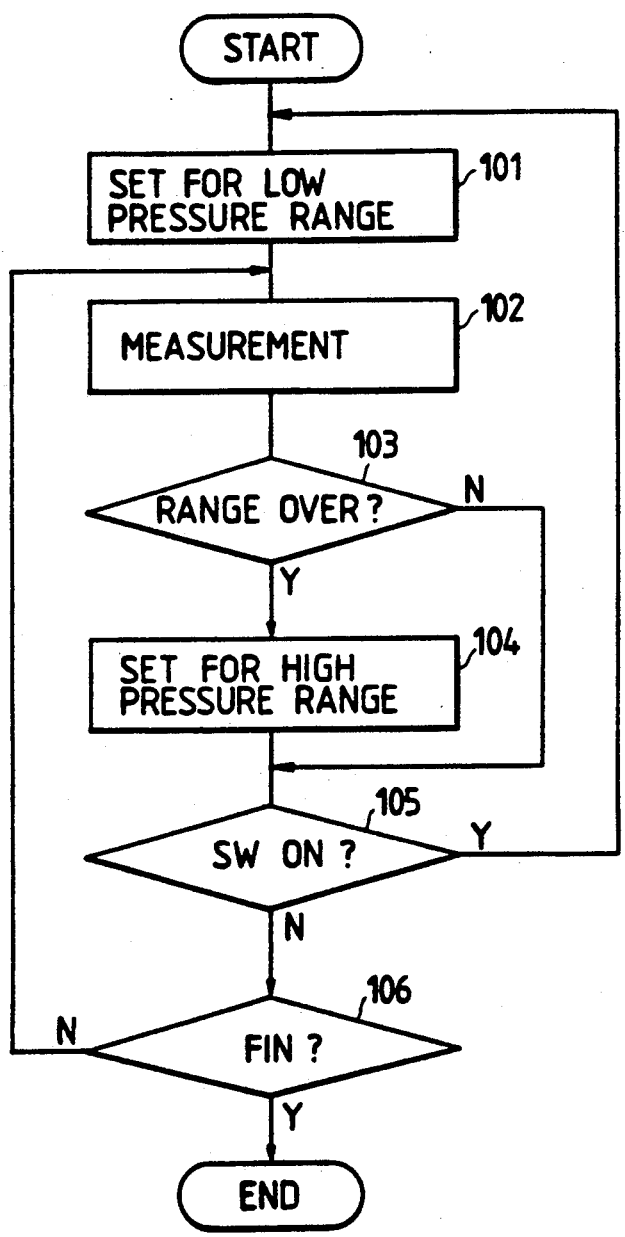
FIG. 5 is a flow chart.

These actions are executed by the MPU 51 operating in accordance with the flow chart of intraocular pressure measurement shown in FIG. 5. That is, with the start of measurement, at step 101, the source resistance is changed over to RH by the analog switch 53 and setting is made to a low pressure range. Subsequently, at step 102, measurement is effected, and at step 103, whether it is range-over is checked from the result of the measurement. If it is not a range-over, advance is made to step 105, and if it is a range-over, at step 104, the source resistance is changed over to RL by the analog switch 53 to set it to a high pressure range. If at step 105, the reset switch 52 is ON, the eye to be examined is determined to have been replaced by another eye, and return is made to step 101. Also, if the reset switch 52 is OFF and measurement is not to be terminated at step 106, return is made to step 102, where measurement is effected in the high pressure range. If measurement is to be terminated at step 106, the measurement is terminated.

Figure 6:
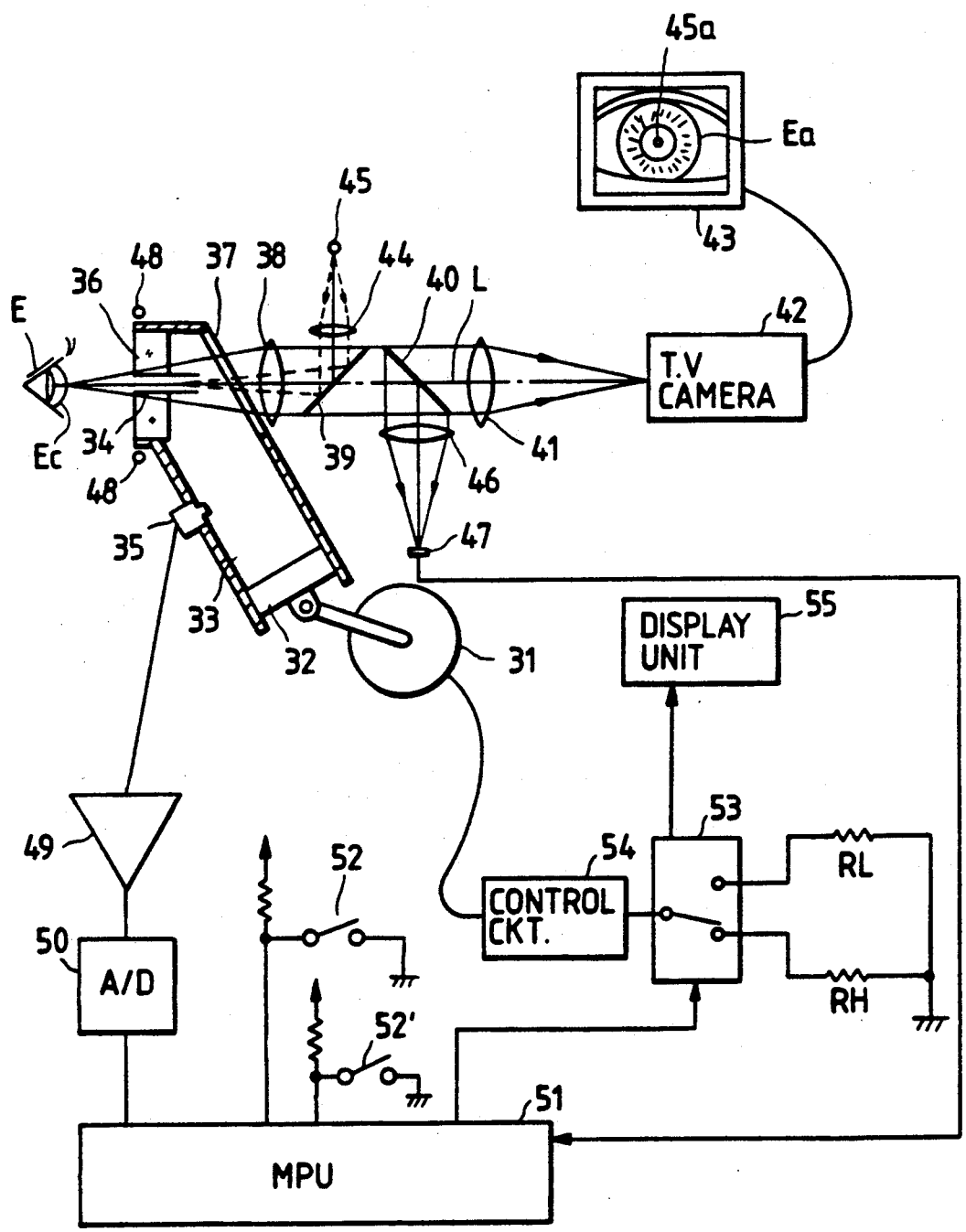
FIG. 6 shows a modification in which a display system is added.

FIG. 6 shows a modification of the FIG. 4 embodiment in which the display of the selection of the measurement range and the display to the effect that the measurement range is a range-over is effected by a display element 55. When the source resistance is set to RH, a green light emitting diode is turned on, and when the source resistance is changed over to RL, a red light emitting diode is turned on. Where measurement cannot be effected in the state in which the source resistance is set to RH, that is, where the measurement range is range-over or alignment is unsatisfactory, the green light emitting diode is turned on and off with the frequency changed, and where measurement cannot be effected (alignment is unsatisfactory) in the state in which the source resistance is set to RL, the red light emitting diode is turned on and off.

When the measurement range is a range-over, it may be displayed by characters (e.g. "over"). By the above-described display, it can be confirmed with the aid of turning on of the green light emitting diode during the change of the eye to be examined that the measurement range is a low pressure range, and the wrong operation of forgetting to depress the reset switch during the change of the eye to be examined and effecting the next measurement without a high pressure range being changed can be prevented. Also, where measurement cannot be effected in spite of alignment being proper with measurement being effected in the low pressure range in which the green light emitting diode is turned on, that is, where the measurement range is a range-over, there takes place the above-mentioned display "over" and immediately after that, the measurement range changes over to the high pressure range and the red light emitting diode is turned on. Also, where the measured value is high when measurement is effected in a measurement range for low intraocular pressure and the change-over of the range is effected through the MPU 51 so that at the next time, the measurement range is a measurement range for high intraocular pressure for the same eye to be examined, change-over takes from the turn-on of the green light emitting diode to the turn-on of the red light emitting diode. Also, where the measured value is low when measurement is effected in a measurement range for high intraocular pressure and the change-over of the range is effected through the MPU 51 so that at the next time, the measurement range is a measurement range for low intraocular pressure for the same eye to be examined, change-over takes from the turn-on of the red light emitting diode to the turn-on of the green light emitting diode. The display element 25 may effectively be a liquid crystal element, an electroluminescence element, an electrochromy element, a photochromy element or the like, and any of these may be a single element, an array element or a matrix element.

As regards the display, use may be made of a change in the luminance of emitted light, besides a change in hues such as green and red. Although the visual display has been described above, at least part of the display may be done by sound. For example, where the measurement range is a range-over, this fact may be indicated by a sound and the selection of the measurement range for low intraocular pressure and the selection of the measurement range for high intraocular pressure may be displayed by the turning on of a green light emitting diode and a red light emitting diode, respectively.

We claim:

1. A non-contact tonometer having:
    fluid projecting means for compressing fluid in a compression chamber and projecting the fluid to the cornea of an eye to be examined located at a predetermined distance therefrom, said fluid projecting means being capable of selecting a first range as a pressurizing range for measurement of intraocular tension and a second range including a value higher than in the degree of pressurization relative to said first range;
    measuring means for detecting a predetermined deformation of the cornea of the eye to be examined caused by the projecting of the compressed fluid and measuring the value of the intraocular tension of the eye to be examined;
    change-over means for changing the pressurizing range for measurement of intraocular tension between said first range and said second range;
    state detecting means for effecting at least one of detection of the fact that measurement is impossible by said measuring means and detection of the replacement of the eye to be examined by another eye; and
    control means for operating said change-over means on the basis of at least one of the output of said state detecting means and the measured value measured by said measuring means.

2. A non-contact tonometer according to claim 1, wherein said state detecting means comprises alignment detecting means, and further comprises means for discriminating whether measurement is impossible within a prescribed time due to unsatisfactory alignment or whether measurement is impossible because the cornea of the eye to be examined does not exhibit the predetermined deformation in spite of satisfactory alignment, and wherein said change-over means changes the pressurizing range in response to said discriminating means discriminating that measurement is impossible because the cornea of the eye to be examined does not exhibit the predetermined deformation in spite of satisfactory alignment in the latter case.

3. A non-contact tonometer according to claim 2, wherein said change-over means produces an output which is transmitted to said control means to change the pressurizing range for measurement of intraocular tension from said first range to said second range.

4. A non-contact tonometer according to claim 2, wherein if said state detecting means detects the replacement of the eye to be examined by another eye and said control means controls said change-over means to return said fluid projecting means to said first range in accordance with the detection of the replacement of the eye by said state detecting means.

5. A non-contact tonometer according to claim 1, wherein said control means control said change-over means to change the pressurizing range in accordance with the magnitude of the measured value measured by said measuring means.

6. A non-contact tonometer according to claim 1, wherein said state detecting means comprises determining means for determining the replacement of the eye to be examined by another eye, and wherein said state detecting means detects from an output of said determining means that the eye to be examined has been replaced by another eye.

7. A non-contact tonometer according to claim 1, wherein said state detecting means comprises a reset switch for resetting said tonometer, wherein said state detecting means detects by the output of said reset switch that the eye to be examined has been replaced by another eye.

8. A non-contact tonometer according to claim 7, wherein said reset switch serves also as the operation starting switch of a printer for recording the result of the measurement of intraocular tension.

9. A non-contact tonometer according to claim 7, wherein said reset switch serves also as a clear switch for clearing the measurement data of intraocular tension in the past.

10. A non-contact tonometer according to claim 1, wherein said change-over means comprises a solenoid for driving a piston in the compression chamber and means to change the circuit resistance of said solenoid.

11. A non-contact tonometer according to claim 1, provided with display means for effecting at least one of the selective display of said first range and said second range and the display of the fact that measurement is impossible by said measuring means because the pressurizing range during measurement is inappropriate.

12. A non-contact tonometer according to claim 11, wherein said display means included visual display means.

13. A non-contact tonometer according to claim 11, wherein said display means includes aural display means.

14. A non-contact tonometer having:
fluid projecting means for compressing fluid in a compression chamber and projecting the fluid to the cornea of an eye to be examined located at a predetermined distance therefrom, said fluid projecting means being capable of selecting a first range as a pressurizing range for measurement of intraocular tension and a second range including a value higher than in the degree of pressurization relative to said first range;

measuring means for detecting a predetermined deformation of the cornea of the eye to be examined caused by said compressed fluid and measuring the value of the intraocular tension of the eye to be examined;

change-over means for changing the pressurizing range for measurement of intraocular tension between said first range and said second range;

state detecting means for effecting the detection of the fact that measurement is impossible by said measuring means and detection of the replacement of the eye to be examined by another eye;

control means for operating said change-over means on the basis of at least one of the output of said state detecting means and the measured value measured by said measuring means; and display means for effecting at least one of the selective display of said first range and said second range and the display of the fact that measurement is impossible by said measuring means because the pressurizing range during measurement is inappropriate.

* * * * *

UNITED STATES PATENT AND TRADEMARK OFFICE
CERTIFICATE OF CORRECTION

PATENT NO. : 5,107,851　　　　　　　　　　Page 1 of 2
DATED　　　 : April 28, 1992
INVENTOR(S) : KOICHI YANO, ET AL.

It is certified that error appears in the above-identified patent and that said Letters Patent is hereby corrected as shown below:

COLUMN 1:

Line 10, "to an eye onto" should read --onto an eye to--.
    Line 30, "of" should be deleted.

COLUMN 3:

Line 37, "passed" should read --passes--.
    Line 54, " awaiting" should read --a waiting--.

COLUMN 4:

Line 24, "to" should be deleted.
    Line 34, "both" should be deleted.
    Line 53, "With" should read --When--.
    Line 54, "restored" should read --restored to--.
    Line 55, "re-" should read --is restored to--.
    Line 56, "stores" should be deleted.
    Line 62, "light" should read --light at that point in time tu--; and after "than", "at that" should be deleted.
    Line 63, "point in time tu" should be deleted.

UNITED STATES PATENT AND TRADEMARK OFFICE
CERTIFICATE OF CORRECTION

PATENT NO. : 5,107,851
DATED : April 28, 1992
INVENTOR(S) : KOICHI YANO, ET AL.

It is certified that error appears in the above-identified patent and that said Letters Patent is hereby corrected as shown below:

<u>COLUMN 9</u>:

Line 16, "control" (second occurrence) should read --controls--.
    Line 35, "the" should read --an--.
    Line 40, "the" should read --previous--.
    Line 41, "in the past." should read --.--.

<u>COLUMN 10</u>:

Line 2, "provided with" should read --further comprising--.
    Line 13, "having:" should read --comprising:--.

Signed and Sealed this

Ninth Day of November, 1993

Attest:

BRUCE LEHMAN

Attesting Officer      Commissioner of Patents and Trademarks